United States Patent [19]

Tyers

[11] Patent Number: 5,330,982
[45] Date of Patent: Jul. 19, 1994

[54] PHARMACEUTICAL COMPOSITION CONTAINING A 5-HT RECEPTOR ANTAGONIST AND AN H+K+ATPASE INHIBITOR AND A METHOD OF TREATING GASTROINTESTINAL DISORDERS THEREWITH

[75] Inventor: Michael B. Tyers, Ware, England

[73] Assignee: Glaxo Group Limited, London, England

[21] Appl. No.: 935,443

[22] Filed: Aug. 25, 1992

Related U.S. Application Data

[63] Continuation of Ser. No. 769,393, Oct. 1, 1991, abandoned, which is a continuation of Ser. No. 537,789, Jun. 14, 1990, abandoned, which is a continuation of Ser. No. 133,893, Dec. 16, 1987, abandoned.

[30] Foreign Application Priority Data

Dec. 17, 1986 [GB] United Kingdom ............... 8630080

[51] Int. Cl.$^5$ ............................................. A61K 31/55
[52] U.S. Cl. ................................. 514/214; 514/299; 514/306; 514/338; 514/413
[58] Field of Search .............. 514/214, 299, 306, 338, 514/413

[56] References Cited

U.S. PATENT DOCUMENTS

| | | | |
|---|---|---|---|
| 4,721,720 | 1/1988 | Wootton et al. | 514/304 |
| 4,753,789 | 6/1988 | Tyers et al. | 424/10 |
| 4,783,478 | 11/1988 | Wootton et al. | 514/397 |
| 4,851,407 | 7/1989 | Wootton et al. | 514/213 |
| 4,929,632 | 5/1990 | Tyers | 514/397 |

FOREIGN PATENT DOCUMENTS

| | | |
|---|---|---|
| 0189002 | 7/1986 | European Pat. Off. ... A61K 31/445 |
| 0215545 | 3/1987 | European Pat. Off. ... A61K 31/445 |
| 0220011 | 4/1987 | European Pat. Off. ... A61K 31/435 |
| 0226266 | 6/1987 | European Pat. Off. ... A61K 31/415 |
| 1525958 | 9/1978 | United Kingdom . |
| 2161160A | 1/1986 | United Kingdom . |

OTHER PUBLICATIONS

Chemical Abstracts, 1985, vol. 102, No. 11, 89907w.
Gastroenterology, 1985:88:64–9, Prichard et al.

Primary Examiner—Marianne M. Cintins
Assistant Examiner—William R. A. Jarvis
Attorney, Agent, or Firm—Bacon & Thomas

[57] ABSTRACT

The invention relates to the use of a compound which is an antagonist of 5-HT at 5-HT$_3$ receptors and promotes gastric emptying in conjunction with an H+K+ATPase inhibitor in the treatment of gastrointestinal disorders.

10 Claims, No Drawings

PHARMACEUTICAL COMPOSITION CONTAINING A 5-HT RECEPTOR ANTAGONIST AND AN H+K+ATPASE INHIBITOR AND A METHOD OF TREATING GASTROINTESTINAL DISORDERS THEREWITH

This is a continuation of application Ser. No. 769,393, filed Oct. 1, 1991, abandoned, which is a continuation of application Ser. No. 537,789, filed Jun. 14, 1990, abandoned, which is a continuation of application Ser. No. 133,893, filed Dec. 16, 1987, abandoned.

This invention relates to improvements in the treatment of gastrointestinal disorders. More particularly it relates to the use of a compound having antagonist activity at 5-$HT_3$ receptors in conjunction with an H+K+ATPase inhibitor in the treatment of such conditions, and to pharmaceutical compositions containing such compounds.

Receptors of the type now designated as 5-$HT_3$ receptors are known in the art as 5-$HT_3$, 5-HT'M' or 5-HT 'M'-like' receptors. Such receptors have been described for example by Fozard et al., Eur. J. Pharmacol., 1979, 59, 195–210; Ireland, Straughan and Tyers, Br. J. Pharmacol., 1982, 75, 16P; Humphrey, Neuropharm. 1984, 23, 1503–1570; Richardson et al., Nature, 1985, 316, 126–131; and Bradley et al., Neuropharm, 1986, 25, 563–576.

5-HT receptors of this type are located, for example, on the terminals of afferent sensory neurones and in the isolated quinea-pig ileum preparation and are also present in the central nervous system. Compounds which act as antagonists of 5-HT at 5-$HT_3$ receptors may be identified using standard tests, for example, in vitro by measuring their inhibition of the depolarising effect of 5-HT on the rat or rabbit isolated vagus nerve, or the tachycardia produced by 5-HT in the rabbit isolated heart or the contraction produced by 5-HT in the guinea-pig isolated ileum, or in vivo by measuring their effect on the Von Bezold-Jarisch reflex (induced by 5-HT) as described, for example, in the above-mentioned references.

A variety of compounds which act as antagonists of 5-HT at 5-$HT_3$ receptors have been described in the art. These compounds are generally azabicyclo derivatives and/or benzoic acid derivatives or imidazole derivatives. The azabicyclo derivatives include compounds containing a bridged piperidyl group, such as a tropyl, pseudotropyl, homotropyl or quinuclidinyl group, and they preferably contain a carbocyclic or heterocyclic aromatic group conjugated, for example as an ester or amide, to the azabicyclic ring. The aromatic group may be for example an optionally substituted phenyl, indolyl, benzofuranyl, benzothienyl, benzisoxazolyl, indazolyl or pyrimidinyl group. The benzoic acid derivatives, which, act as antagonists of 5-HT at 5-$HT_3$ receptors include benzoates and benzamides, for example esters or amides formed with an azabicyclic group as defined above, or formed with a piperidyl group.

Such compounds have been disclosed inter alia in published UK Patent Applications Nos. 2100259, 2125398, 2131420, 2132189, 2145416, 2152049, 2153821 and 2169292, published European Patent Applications Nos. 111608, 116255, 158265, 191562, 210840, 214772, 219193, 221702, 226267, 227215, 230718, 235878 and 242973, and published Australian Patent Application No. 87/67121. The compounds disclosed in published European Patent Applications Nos. 13138, 67615, and 94742 have also been described as antagonists of 5-HT at 5-$HT_3$ receptors, in published European Patent Applications Nos. 215545 and 220011. In addition, 4-amino-N-1-azabicyclo[2.2.2]oct-3-yl-5-chloro-2-methoxybenzamide (also known as zacopride), described in European Patent Specification No. 99789, has also now been shown to be an antagonist of 5-HT at 5$HT_3$ receptors.

One of the commonly occurring properties of compounds which are antagonists of 5-HT at 5-$HT_3$ receptors is that they promote gastric emptying. Compounds which are antagonists of 5-HT at 5-$HT_3$ receptors and promote gastric emptying may be used in the treatment of conditions which are relieved by the promotion of gastric emptying. Such conditions include gastrointestinal disorders such as gastric stasis, and symptoms of gastrointestinal dysfunction such as dyspepsia, peptic ulcer, reflux oesophagitis and flatulence.

Compounds which inhibit the action of the gastric proton pump H+K+ adenosinetriphosphatase (ATPase) may be used in the treatment of conditions where there is an advantage in lowering gastric acidity. Such conditions include duodenal and gastric ulceration, reflux oesophagitis and Zollinger-Ellison syndrome.

The combination of a 5-$HT_3$ receptor antagonist which promotes gastric emptying with an H+K+ATPase inhibitor provides a useful and advantageous combination for the treatment of gastrointestinal disorders. Administration of such a 5-$HT_3$ receptor antagonist and an H+K+ATPase inhibitor is particularly useful for the treatment of conditions such as reflux oesophagitis where the promotion of gastric emptying serves to alleviate the reflux, thereby encouraging the healing effect of the H+K+ATPase inhibitor. Co-administration of a 5-$HT_3$ receptor antagonist and an H+K+ATPase inhibitor may also be useful in general anaesthesia. More particularly, when the two compounds are given before or during anaesthesia, the promotion of gastric emptying by the 5-$HT_3$ antagonist and the reduction of gastric acid production by the H+K+ATPase inhibitor prevent both acid inhalation during anaesthesia and post-anaesthetic nausea and vomiting. Co-administration of an 5-$HT_3$ receptor antagonist and an H+K+ATPase inhibitor may also be useful for the treatment of irritable bowel syndrome.

The present invention thus provides a method of treating gastrointestinal disorders which comprises administering to a human or animal subject a compound which is an antagonist of 5-HT at 5-$HT_3$ receptors and promotes gastric emptying, in conjunction with an H+K+ATPase inhibitor.

According to another aspect the invention provides for the use of a 5-$HT_3$ receptor antagonist which promotes gastric emptying, in the manufacture of a medicament for administration in conjunction with an H+K+ATPase inhibitor, in the treatment of gastrointestinal disorders.

The 5-$HT_3$ receptor antagonist and the H+K+ATPase inhibitor may be administered as a single pharmaceutical composition comprising effective amounts of the two active ingredients. Alternatively the two active ingredients may be co-administered in the form of two separate pharmaceutical compositions for simultaneous or sequential use.

Where appropriate, the 5-$HT_3$ receptor antagonist and/or the H+K+ATPase inhibitor may be administered in the form of a physiologically acceptable salt or solvate e.g. hydrate. Suitable salts include acid addition salts formed with organic or inorganic acids, for example hydrochlorides, hydrobromides, phosphates, citrates, acetates, maleates and tartrates. It may also be appropriate to administer the H+K+ATPase inhibitor in the form of an alkaline salt, such as an alkali metal, alkaline earth metal, quaternary ammonium or quanidinium salt.

The use of physiologically acceptable equivalents of the 5-HT$_3$ receptor antagonist, i.e. physiologically acceptable compounds which are converted in vivo into the parent compound, and solvates (e.g. hydrates) is also included within the scope of the invention.

Preferred classes of 5-HT$_3$ receptor antagonists for use in the present invention include 3-(imidazol-1-yl) methyltetrahydrocarbazolones, 3-(imidazol-4-yl)-(indol-3-yl)-1-propanones, azabicyclo derivatives (e.g. containing a bridged piperidyl group such as a tropyl, pseudotropyl, homotropyl or quinuclidinyl group) and benzoic acid derivatives (e.g. benzoates and benzamides).

Particular mention may be made of the compounds which act as antagonists of 5-HT at 5-HT$_3$ receptors disclosed in published UK Patent Specifications Nos. 2100259, 2125398, 2131420, 2132189, 2145416, 2152049, 2153821 and 2169292, published European Patent Specifications Nos. 13138, 67615, 94742, 99789, 111608, 116255, 158265, 191562, 210840, 214772, 219193, 221702, 226267, 227215, 230718, 235878 and 242973, and published Australian Patent Application No. 87/67121.

Preferred compounds for use according to the invention are those compounds which act as antagonists of 5-HT at 5-HT$_3$ receptors described in published UK Patent Specification Nos. 2100259, 2132189, 2125398, 2152049 and 2153821, published European Patent Specification Nos. 13138, 94742, 99789, 116255, 221702, 226267, 235878 and 242973 and published Australian Patent Application No. 87/67121.

Particularly preferred compounds for use according to the present invention are those described in published UK Patent Specification No. 2153821. Further particularly preferred compounds for use according to the invention are those described in published UK Patent Specifications Nos. 2100259 and 2125398 and published European Patent Specifications Nos. 94742 and 242973. Yet another particularly preferred compound for use according to the invention is zacopride.

A preferred group of compounds for use according to the invention, described in UK Specification No. 2125398, may be represented by the general formula (I):

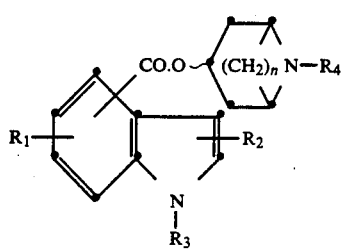

(I)

wherein R$_1$ and R$_2$ independently represent hydrogen, halogen, C$_{1-4}$alkyl, C$_{1-4}$ alkoxy, hydroxy, amino, C$_{1-4}$ alkylamino, di(C$_{1-4}$)alkylamino, mercapto or C$_{1-4}$ alkylthio; R$_3$ represents hydrogen, C$_{1-4}$ alkyl, C$_{3-5}$ alkenyl, aryl or aralkyl; R$_4$ represents hydrogen, C$_{1-7}$ alkyl, C$_{3-5}$ alkenyl or aralkyl; n is 2 or 3; the free valence is attached to either fused ring, and the azabicyclic ring is in either the exo or endo configuration; and acid addition salts and quaternary ammonium salts thereof.

In the compounds of formula (I) R$_1$ and R$_2$ may, for example, independently represent hydrogen, halogen or C$_{1-4}$ alkyl, R$_3$ may be, for example, hydrogen or C$_{1-4}$ alkyl and R$_4$ may be, for example, hydrogen, C$_{1-7}$ alkyl or aralkyl; the carbonyl group is preferably attached to the 3-position of the indole ring, and the azabicyclic ring is preferably in the endo configuration.

Another preferred group of compounds according to the present invention, described in UK Specification No. 2100259, may be represented by the general formula (II):

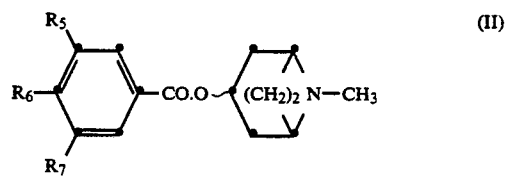

(II)

wherein R$_5$ represents C$_{1-4}$ alkyl, C$_{1-4}$ alkoxy, or halogen; and R$_6$ and R$_7$ independently represent hydrogen, C$_{1-4}$ alkyl, C$_{1-4}$ alkoxy or halogen provided that R$_6$ is hydrogen when R$_7$ is hydrogen; and pharmaceutically acceptable salts thereof.

A preferred class of compounds of formula (II) are those in which R$_5$ and R$_7$ are the same and each represents methyl, methoxy or chlorine, and R$_6$ represents hydrogen.

A further preferred group of compounds for use according to the invention, described in European Specification No. 94742, may be represented by the general formula (III):

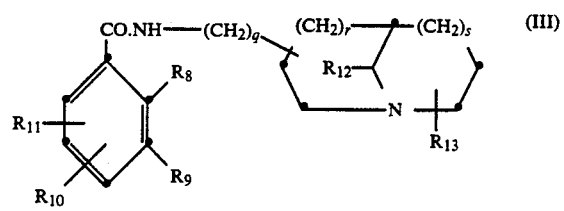

(III)

wherein R$_8$ represents a C$_{1-6}$ alkoxy or amino N-substituted by one or two groups selected from C$_{1-6}$ alkyl or C$_{3-8}$ cycloalkyl or optionally N-substituted by C$_{4-5}$ polymethylene; one of R$_9$, R$_{10}$ and R$_{11}$ is hydrogen and the other two are independently selected from hydrogen, chloro, bromo, trifluoromethyl, hydroxy, C$_{1-6}$ alkoxy, C$_{1-6}$ alkylthio, C$_{1-6}$ alkyl and amino; one of R$_{12}$ and R$_{13}$ represents hydrogen, C$_{1-6}$ alkyl, phenyl or phenylC$_{1-3}$alkyl, which phenyl moieties may be substituted by C$_{1-6}$ alkyl, C$_{1-6}$ alkoxy, CF$_3$ or halogen, and the other of R$_{12}$ and R$_{13}$ is hydrogen or C$_{1-6}$ alkyl; q is zero or an integer from 1 to 4; r is zero, or an integer from 1 to 3; and s is zero, 1 or 2.

Preferred compounds of formula (III) are those wherein R$_8$ is methoxy, R$_9$ is hydrogen, R$_{10}$ is 4-amino, R$_{11}$ is 5-chloro (relative to the benzamide group), R$_{12}$ and R$_{13}$ independently represent hydrogen or C$_{1-6}$ alkyl; q is zero, r is 1 or 2 and s is zero, 1 or 2.

Yet another preferred group of compounds for use according to the invention, described in our UK Patent Specification No. 2153821 and European Specifications Nos. 191562, 210840 and 219193, may be represented by the general formula (IV):

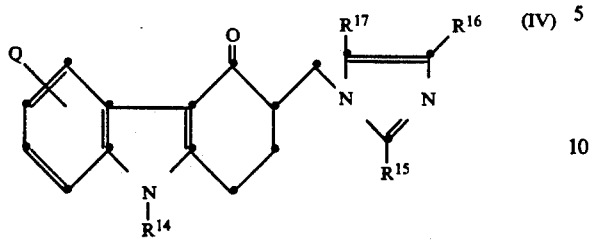

wherein $R^{14}$ represents a hydrogen atom or a group selected from $C_{1-10}$alkyl, $C_{3-6}$ alkenyl, $C_{3-10}$ alkynyl, $C_{3-7}$cycloalkyl, $C_{3-7}$cycloalkyl$C_{1-4}$alkyl, phenyl or phenyl$C_{1-3}$alkyl, and in the case where Q represents a hydrogen atom, $R^{14}$ may also represent $—CO_2R^{18}$, $—COR^{18}$, $—CONR^{18}R^{19}$ or $—SO_2R^{18}$ (wherein $R^{18}$ and $R^{19}$, which may be the same or different, each represents a hydrogen atom, a $C_{1-6}$ alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^{18}$ does not represent a hydrogen atom when $R^{14}$ represents a group $—CO_2R^{18}$ or $—SO_2R^{18}$); one of the groups represented by $R^{15}$, $R^{16}$ and $R^{17}$ is a hydrogen atom or a $C_{1-6}$ alkyl, $C_{3-7}$cycloalkyl, $C_{2-6}$alkenyl, or phenyl$C_{1-3}$alkyl group, and each of the other two groups, which may be the same or different, represents a hydrogen atom or a $C_{1-6}$ alkyl group; Q represents a hydrogen atom or a halogen atom or a hydroxy, $C_{1-4}$alkoxy, phenyl$C_{1-3}$alkoxy or $C_{1-6}$ alkyl group or a group $—NR^{20}R^{21}$ or $—CONR^{20}R^{21}$ (wherein $R^{20}$ and $R^{21}$, which may be the same or different, each represents a hydrogen atom or a $C_{1-4}$ alkyl or $C_{3-4}$ alkenyl group, or together with the nitrogen atom to which they are attached form a saturated 5 to 7 membered ring); and physiologically acceptable salts and solvates thereof.

A particularly preferred class of compounds for use according to the present invention are those represented by the formula (IV) wherein $R^{14}$ represents a hydrogen atom or a methyl, ethyl, propyl, prop-2-yl, prop-2-enyl or cyclopentyl group; $R^{16}$ represents a hydrogen atom; and either $R^{15}$ represents a methyl, ethyl, propyl or prop-2-yl group and $R^{17}$ represents a hydrogen atom or $R^{15}$ represents a hydrogen atom and $R^{17}$ represents a methyl or ethyl group; and Q represents a hydrogen atom.

A still further preferred group of compounds for use according to the invention, described in European Patent Specification No. 242973, may be represented by the general formula (V):

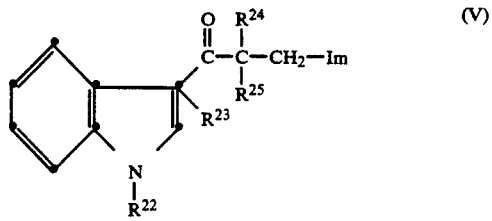

wherein Im represents an imidazolyl group of formula:

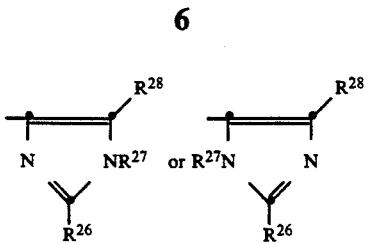

$R^{22}$ represents a hydrogen atom or a $C_{1-6}$ alkyl, $C_{3-6}$ alkenyl, $C_{3-10}$alkynyl, $C_{3-7}$ cycloalkyl, $C_{3-7}$ cycloalkyl$C_{1-4}$alkyl, phenyl or phenyl$C_{1-3}$alkyl group; $R^{23}$ represents a hydrogen atom or a $C_{1-6}$ alkyl, $C_{3-6}$ alkenyl, $C_{3-7}$cycloalkyl, phenyl or phenyl$C_{1-3}$alkyl group; $R^{24}$ and $R^{25}$, which may be the same or different, each represents a hydrogen atom or a $C_{1-6}$ alkyl group; one of the groups represented by $R^{26}$, $R^{27}$ and $R^{28}$, is a hydrogen atom or a $C_{1-6}$ alkyl, $C_{3-7}$ cycloalkyl, $C_{3-6}$ alkenyl, phenyl or phenyl$C_{1-3}$alkyl group, and each of the other two groups, which may be the same or different, represents a hydrogen atom or a $C_{1-6}$ alkyl group; and physiologically acceptable salts and solvates thereof.

A preferred class of compounds represented by the formula (V) for use according to the present invention are those wherein $R^{22}$ represents a hydrogen atom or a methyl, prop-2-enyl or cyclopentyl group; $R^{23}$ represents a hydrogen atom or a methyl group; $R^{24}$ and $R^{25}$ each independently represent a hydrogen atom or a methyl group; $R^{26}$ and $R^{27}$ each represent a hydrogen atom; and $R^{28}$ represents a hydrogen atom or a $C_{1-3}$ alkyl group, most preferably methyl.

Another preferred group of compounds for use according to the invention, described in European Specification No. 235878 and Australian Specification No. 87/67121, may be represented by the general formulae (VI) and (VII) respectively:

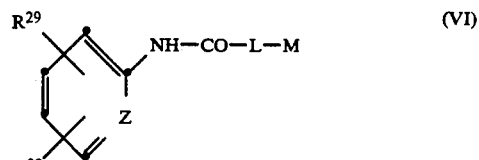

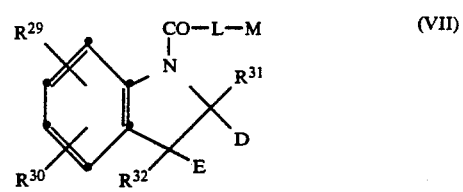

wherein L is NH or 0; $R^{29}$ and $R^{30}$ are independently selected from hydrogen, halogen, $CF_3$, $C_{1-6}$alkyl, $C_{1-6}$ alkoxy, $C_{1-6}$alkylthio, $C_{1-7}$acyl, $C_{1-7}$acylamino, $C_{1-6}$alkylsulphonylamino, N-($C_{1-6}$ alkylsulphonyl)-N-$C_{1-4}$alkylamino, $C_{1-6}$alkylsulphinyl, hydroxy, nitro or amino, aminocarbonyl, aminosulphonyl, aminosulphonylamino or N-(aminosulphonyl)-$C_{1-4}$alkylamino optionally N-substituted by one or two groups selected from $C_{1-6}$alkyl, $C_{3-8}$ cycloalkyl, $C_{3-8}$ cycloalkyl$C_{1-4}$ alkyl, phenyl or phenyl$C_{1-4}$ alkyl groups or optionally N-disubstituted by $C_{4-5}$polymethylene; Z is a moiety capable of hydrogen bonding to the NH group depicted in formula (VI); D and E are independently selected from hydrogen or $C_{1-4}$alkyl, or together are a bond; $R^{31}$ and $R^{32}$ are independently selected from hydrogen, $C_{1-6}$ alkyl, $C_{2-6}$alkenyl$C_{1-4}$alkyl, or together are $C_{2-4}$ polymethylene; M is a group of formula (a), (b) or (c):

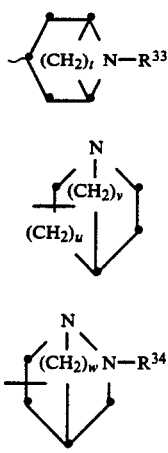

wherein t is 2 or 3; u is 1 or 2; v is 1 to 3; w is 1 to 3; and $R^{33}$ or $R^{34}$ is $C_{1-7}$alkyl, $C_{3-8}$cycloalkyl, $C_{3-8}$cycloalkyl$C_{1-2}$alkyl or $C_{2-7}$alkenyl$C_{1-4}$alkenyl; and pharmaceutically acceptable salts thereof.

Preferably L is NH; $R^{29}$ is often hydrogen and $R^{30}$ is hydrogen or a 4-substituent such as halo or methoxy; Z is preferably C—OCH$_3$, C—OC$_2$H$_5$, C—OC$_3$H$_7$, C—CO$_2$CH$_3$, C—CO$_2$C$_2$H$_5$ or SO$_2$N(CH$_3$)$_2$; often D and E are both hydrogen; often $R^{31}$ and $R^{32}$ are both hydrogen; preferably t is 2 or 3 and u, v and w are 1 or 2; and $R^{33}/R^{34}$ is preferably methyl or ethyl, most preferably methyl.

Yet another preferred group of compounds for use according to the invention, described in UK Specification No. 2152049, may be represented by the general formula (VIII):

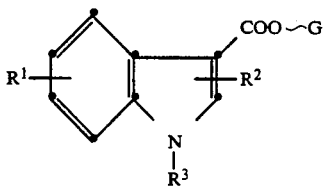

wherein $R^1$, $R^2$ and $R^3$ are as defined for general formula (I) and G is a group of formula (d) or (e):

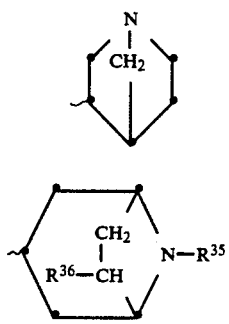

wherein $R^{35}$ is $C_{1-4}$ alkyl and $R^{36}$ is methoxy; and pharmaceutically acceptable salts thereof.

A particularly preferred 5-HT$_3$ receptor antagonist for use according to the present invention is 1,2,3,9-tetrahydro-9-methyl-3-[(2-methyl-1H-imidazol-1-yl)methyl]-4H-carbazol-4-one. A preferred form of this compound is the hydrochloride, particularly in hydrated form, e.g. the dihydrate.

Further particularly preferred compounds for use according to the present invention are (3α-tropanyl)-1H-indole-3-carboxylic acid ester; and (+)-endo-4-amino-5-chloro-2-methoxy-N-(1-azabiyclo)-[3.3.1]-non-4-yl) benzamide, and their physiologically acceptable salts and solvates. A particularly preferred from of the last named compound is its hydrochloride hydrate.

Other preferred compounds for use according to the present invention are:

3-(5-methyl-1H-imidazol-4-yl)-1-(1-methyl-1H-indol-3-yl)-1-propanone;

4-amino-N-1-azabicyclo[2.2.2]oct-3-yl-5-chloro-2-methoxybenzamide;

1αH, 3α,5αH-tropan-3-yl-3,5-dimethylbenzoate;

1αH,3α,5αH-tropan-3-yl-3,5-dichlorobenzoate;

indole-[5-(2-methyl-2-azabicyclo(2.2.2)octyl]-3-carboxylate;

1H-indol-3-yl-carboxylic acid (3R*,4S*)-1-azabicyclo-[2.2.1]hept-3-yl ester;

1H-indolyl-3-carboxylic acid 2S-(1-methyl-2-pyrrolidinylmethyl) ester;

4-amino-5-chloro-2-methoxy-N-(3-quinuclidinylmethyl)benzamide;

(±)4-amino-5-chloro-2-methoxy-N-(6'α-[4'-thia-1'-azabicyclo[3,3,1]nonyl])benzamide;

(±)4-amino-5-chloro-2-methoxy-N-(6'α-[4'-oxa-1'-azabicyclo[3,3,1]nonyl])benzamide;

and physiologically acceptable salts and solvates thereof.

Suitable H+K+ATPase inhibitors for use according to the present invention include tetrahydrothiophenes (e.g. pyridyl-2-tetrahydrothiophenes), imidazopyridines, benzoxazoles, benzthiazoles and, more particularly, benzimidazole derivatives. Examples of suitable benzimidazole derivatives include 2-(arylmethylsulphinyl) benzimidazoles (e.g. 2-[(amino-substituted phenyl)-methylsulphinyl]benzimidazoles), 2-(pyridylmethylthio) benzimidazoles, 2-(heterocyclicmethylsulphinyl)benzimidazoles and, more particularly, 2-(pyridylmethylsulphinyl)benzimidazoles. Such compounds are disclosed in for example UK Patent Specifications Nos. 1525958 and 2161160, and in European Patent Specifications Nos. 5129, 150586, 220053 and 221041. Particular examples of benzimidazole derivatives which are H+K+ATPase inhibitors are omeprazole, timoprazole, picoprazole and disuprazole.

The dose at which the 5-HT$_3$ receptor antagonist and H+K+ATPase inhibitor may be administered to man will depend upon the route of administration, the body weight of the patient, the condition being treated and its severity, and the potency of the compounds.

The H+K+ATPase inhibitor may conveniently be administered at doses within the normal dosage range at which the compound is therapeutically effective. Thus, dependent on the influencing factors referred to above, the H+K+ATPase inhibitor may be administered at doses up to, for example, 100 to 500 mg per day. A composition for use according to the invention may contain for example 5-250 mg of the H+K+ATPase inhibitor per dosage unit. Lower unit doses such as 5-100 mg or 5-60 mg (e.g. 10-60 mg) may, however, be appropriate for more potent H+K+ATPase inhibitors.

The 5-HT$_3$ receptor antagonist may in general be administered to man (of approximately 70 kg body weight) at a dose within the ranges specified in the aforementioned patent specifications for the compounds concerned, or at lower doses for example 0.5 μg to 20 mg, preferably 0.05 to 10 mg per unit does which may be administered, for example, 1 to 4 times per day.

Thus a composition for use according to the invention containing a compound of formula (I) as herein defined may contain from 0.2 to 250 mg of the active ingredient per unit dose, and may be administered for example up to four times per day, such that the overall daily dose is in the range 0.5 to 500 mg.

A composition for use according to the invention containing a compound of formula (II) as herein defined may contain from about 0.5 to 100 mg of the active ingredient per unit dose, usually 1 to 50 mg and preferably 3 to 30 mg, and may be adminstered, for example, from 1 to 4 times per day.

A composition for use according to the invention containing a compound of formula (III) as herein defined may contain 0.1 to 20 mg of the active ingredient per unit dose, for example 0.5 to 10 mg, and may be administered, for example, up to six times per day, such that the total daily dose is normally in the range 0.01 to 10 mg/kg.

A composition for use according to the invention containing a compound of formula (IV) as herein defined may contain 0.05 to 25 mg, more preferably 0.05 to 20 mg, of the active ingredient per unit dose, and most preferably 0.1 to 10 mg, and may be administered 1 to 4 times per day.

A composition for use according to the invention containing a compound of formula (V) as herein defined may contain 0.001 to 100 mg of the active ingredient per unit dose, preferably 0.01 to 50 mg, and may be administered 1 to 4 times per day. This dosage is also applicable to zacopride.

A composition for use according to the invention containing of a compound of formula (VI) as herein defined may contain 0.05 to 1000 mg of the active ingredient per unit dose, for example 0.1 to 500 mg, and may be administered, for example, 1 to 4 times per day, such that the total daily dose is in the range 0.0001 to 50 mg/kg, more usually 0.0002 to 25 mg/kg.

A composition for use according to the invention containing a compound of formula (VII) as herein defined may contain 0.05 to 1000 mg of the active ingredient per unit dose, for example 0.5 to 500 mg, and may be administered, for example, 1 to 4 times per day, such that the total daily dose is in the range 0.0001 to 50 mg/kg, more usually 0.0002 to 25 mg/kg.

A composition for use according to the invention containing a compound of formula (VIII) as herein defined may contain from 0.1 to 250 mg of the active ingredient per unit dose, and may be administered up to four times per day, such that the overall daily dose is in the range 0.5 to 500 mg.

According to a particular embodiment of the invention, the 5-HT receptor antagonist 1,2,3,9-tetrahydro-9-methyl-3-[(2-methyl-1H-imidazol-1-yl)methyl]-4H-carbazol-4-one or a physiologically acceptable salt or solvate thereof, at a unit dose of 0.05 to 25 mg (expressed as the weight of free base), may be administered in conjunction with an H+K+ATPase inhibitor at a unit dose of 5 to 250 mg, as either two separate preparations or a single composition. Alternatively the 5-HT$_3$ receptor antagonist component may be a compound of formula (I) as herein defined (e.g. (3α-tropanyl)-1H-indole-3-carboxylic acid ester) administered at a unit dose of 0.2 to 250 mg, or a compound of formula (III) as herein defined (e.g. (±-endo-4-amino-5-chloro-2-methoxy-N-(1-azabicyclo)-[3.3.1]-non-4-yl) benzamide) administered at a unit dose of 0.1 to 20 mg.

According to a further aspect the invention provides a pharmaceutical composition, for use in human or veterinary medicine, comprising effective amounts of a 5-HT$_3$ receptor antagonist which promotes gastric emptying and an H+K+ATPase inhibitor.

Compositions containing the 5-HT$_3$ receptor antagonist in the form of a physiologically acceptable salt, a physiologically acceptable equivalent (as defined above) or a solvate, and/or the H+K+ATPase inhibitor in the form of a physiologically acceptable salt are also included within this aspect of the invention.

Compositions according to the invention may be formulated in conventional manner using one or more physiologically acceptable carriers or excipients. Thus the compositions may be formulated for oral, buccal, parenteral or rectal administration.

Particularly useful pharmaceutical compositions for use according to the invention are those in a form suitable for oral administration.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of one or both active ingredients.

For buccal administration the compositions may take the form of tablets or lozenges formulated in conventional manner.

For parenteral administration the compositions may be presented in a form suitable for bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredients may be in powder form for constitution with a suitable vehicle, e.g. sterile pyrogen-free water, before use.

For rectal administration the compositions may be formulated as suppositories or retention enemas, e.g. containing conventional suppository bases such as cocoa butter or other glycerides.

In addition to the formulations described previously, the compositions according to the invention may also take the form of depot preparations. Such long acting formulations may be administered by implantation (for example subcutaneously or intramuscularly) or by intramuscular injection. Thus, for example, the active ingredients may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions of the invention containing the two active ingredients may be prepared according to conventional techniques well known in the pharmaceutical industry. Thus, for example, the 5-HT$_3$ receptor antagonist and the H+K+ATPase inhibitor may be admixed together with suitable excipients. Tablets excipients. Tablets may be prepared, for example, by direct compression of such a mixture. Capsules may be prepared by filling the blend along with suitable excipients into gelatin capsules, using a suitable filling machine. Controlled release forms for oral or rectal administration may be formulated in a conventional manner associated with controlled release forms.

The compositions for use according to the invention may, if desired, be presented in a pack or dispenser device which may contain one or more unit dosage forms containing the active ingredients. The pack may for example comprise metal or plastic foil, such as a blister pack. The pack or dispenser device may be accompanied by instructions for administration. Where the 5-HT$_3$ receptor antagonist and the H+K+ATPase inhibitor are intended for administration as two separate compositions these may be presented in the form of, for example, a twin pack.

The following example illustrates pharmaceutical compositions according to the invention, containing 1,2,3,9-tetrahydro-9-methyl-3-[(2-methyl-1H-imidazol-1-yl)methyl]-4H-carbazol-4-one hydrochloride dihydrate (Compound A) and omeprazole as the active ingredients. Other 5-HT$_3$ receptor antagonists for use according to the invention and/or other H+K+ATPase inhibitors may be formulated in a similar manner.

Tablets for Oral Administration

Tablets may be prepared by the normal methods such as direct compression or wet granulation.

The tablets may be film coated with suitable film forming materials, such as hydroxypropyl methylcellulose, using standard techniques.

| Direct Compression Tablets | mg/tablet |
| --- | --- |
| (i) Compound A | 5.00* |
| Omeprazole | 30.00 |
| Microcrystalline cellulose NF | 70.00 |
| Anhydrous lactose NF | 44.25 |
| Magnesium stearate BP | 0.75 |
| Compression weight | 150.00 |
| *Equivalent to 4.00 mg free base | |
| (ii) Compound A | 10.0* |
| Omeprazole | 10.0 |
| Microcrystalline cellulose NF | 139.0 |
| Anhydrous lactose NF | 40.0 |

| Direct Compression Tablets | mg/tablet |
| --- | --- |
| Magnesium stearate BP | 1.0 |
| Compression weight | 200.0 |

*Equivalent to 8.0 mg free base.

Compound A and the omeprazole are blended with the excipients. The resultant mix is compressed into tablets using a suitable tablet press fitted with 8.0 mm normal concave punches.

| Wet Granulation Tablet | mg/tablet |
| --- | --- |
| Compound A | 10.0 |
| Omeprazole | 10.0 |
| Lactose BP | 148.0 |
| Starch BP | 20.0 |
| Pregelatinised Maize Starch BP | 10.0 |
| Magnesium Stearate BP | 2.0 |
| Compression Weight | 200.0 |

The active ingredients are sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 8 mm diameter punches.

Tablets of other strengths and/or combination of doses may be prepared by appropriate alterations in the amounts of the active ingredients and the excipients and using punches to suit.

Syrup

This may be either a sucrose or sucrose free presentation.

| A. Sucrose Syrup | mg/5 ml dose |
| --- | --- |
| Compound A | 10.0 |
| Omeprazole | 10.0 |
| Sucrose BP | 2750.0 |
| Glycerine BP | 500.0 |
| Buffer | |
| Flavour | |
| Colour | as required |
| Preservative | |
| Purified Water BP to | 5.0 ml |

The active ingredients, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-Free | mg/5 ml dose |
| --- | --- |
| Compound A | 10.0 |
| Omeprazole | 10.0 |
| Hydroxypropylmethylcellulose USP (viscosity type 4000) | 22.5 |
| Buffer | |
| Flavour | |
| Colour | As required |
| Preservative | |
| Sweetener | |
| Purified Water BP to | 5.0 ml |

The hydroxypropylmethylcellulose is dispersed in hot water, cooled and then mixed with an aqueous solution containing the active ingredients and the other components of the formulation. The resultant solution is adjusted to volume and mixed. The syrup is clarified by filtration.

I claim:

1. A pharmaceutical composition for use in human or veterinary medicine comprising an effective amount of a compound which is an antagonist of 5-HT at 5-HT$_3$ receptors and promotes gastric emptying, and an effective amount of a compound which is an H+K+ATPase inhibitor, with at least one physiologically acceptable carrier or excipient, wherein said compound which is an antagonist of 5-HT at 5-HT$_3$ receptors is a compound of formula (III):

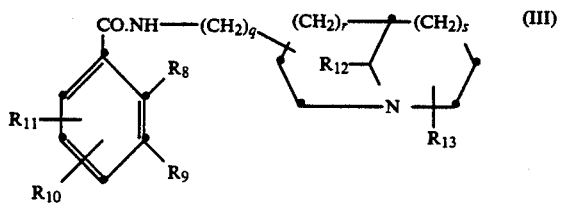

wherein $R_8$ represents a $C_{1-6}$alkoxy or amino N-substituted by one or two groups selected from $C_{1-6}$alkyl and $C_{3-8}$cycloalkyl, or optionally N-substituted by $C_{4-5}$polymethylene; one of $R_9$, $R_{10}$ and $R_{11}$ is hydrogen and the other two are independently selected from hydrogen, chloro, bromo, trifluoromethyl, hydroxy, $C_{1-6}$alkoxy, $C_{1-6}$alkylthio, $C_{1-6}$alkyl and amino; one of $R_{12}$ and $R_{13}$ represents hydrogen, $C_{1-6}$alkyl, phenyl or phenyl$C_{1-3}$alkyl, which phenyl moieties may be substituted by $C_{1-6}$alkyl, $C_{1-6}$alkoxy, $CF_3$ or halogen, and the other of $R_{12}$ and $R_{13}$ is hydrogen or $C_{1-6}$alkyl; q is zero or an integer from 1 to 4; r is zero, or an integer from 1 to 3; and s is zero, 1 or 2, or a physiologically acceptable salt or solvate thereof, and said H+K+ATPase inhibitor is a 2-(pyridylmethylsulphinyl)benzimidazole, or a physiologically acceptable salt thereof.

2. A pharmaceutical composition according to claim 1 wherein said compound which is an antagonist of 5-HT at 5-HT$_3$ receptors is (±)-endo-4-amino-5-chloro-2-methoxy-N-(1-azabicyclo)-[3.3.1]-non-4-yl)benzamide, or a physiologically acceptable salt or solvate thereof.

3. A pharmaceutical composition according to claim 1 wherein said H+K+ATPase inhibitor is omeprazole.

4. A pharmaceutical composition according to claim 1 wherein said compound which is an antagonist of 5-HT at 5-HT$_3$ receptors is (±)-endo-4-amino-5-chloro-2-methoxy-N-(1-azabicyclo)-[3.3.1]-non-4-yl)benzamide, or a physiologically acceptable salt or solvate thereof, and wherein said H+K+ATPase inhibitor is omeprazole.

5. A method of treating gastrointestinal disorders which comprises administering to a human or animal subject in need thereof an effective amount of a compound which is an antagonist of 5-HT at 5-HT$_3$ receptors and promotes gastric emptying in conjunction with an effective amount of a compound which is an H+K+ATPase inhibitor, wherein said compound which is an antagonist of 5-HT at 5-HT$_3$ receptors is a compound of formula (III):

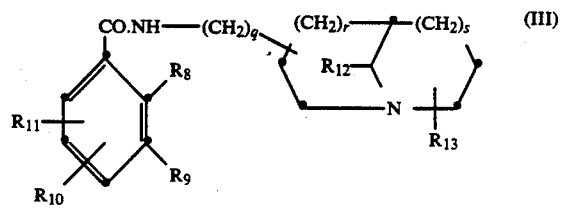

wherein $R_8$ represents a $C_{1-6}$alkoxy or amino N-substituted by one or two groups selected from $C_{1-6}$alkyl and $C_{3-8}$cycloalkyl, or optionally N-substituted by $C_{4-5}$polymethylene; one of $R_9$, $R_{10}$ and $R_{11}$ is hydrogen and the other two are independently selected from hydrogen, chloro, bromo, trifluoromethyl, hydroxy, $C_{1-6}$alkoxy, $C_{1-6}$alkylthio, $C_{1-6}$alkyl and amino; one of $R_{12}$ and $R_{13}$ represents hydrogen, $C_{1-6}$alkyl, phenyl or phenyl$C_{1-3}$alkyl, which phenyl moieties may be substituted by $C_{1-6}$alkyl, $C_{1-6}$alkoxy, $CF_3$ or halogen, and the other of $R_{12}$ and $R_{13}$ is hydrogen or $C_{1-6}$alkyl; q is zero or an integer from 1 to 4; r is zero, or an integer from 1 to 3; and s is zero, 1 or 2, or a physiologically acceptable salt or solvate thereof, and said H+K+ATPase inhibitor is a 2-(pyridylmethylsulphinyl)benzimidazole, or a physiologically acceptable salt thereof.

6. A method according to claim 5 wherein said compound which is an antagonist of 5-HT at 5-HT$_3$ receptors is (±)-endo-4-amino-5-chloro-2-methoxy-N-(1-azabicyclo)-[3.3.1]-non-4-yl)benzamide, or a physiologically acceptable salt or solvate thereof.

7. A method according to claim 5 wherein said H+K+ATPase inhibitor is omeprazole.

8. A method according to claim 5 wherein said compound which is an antagonist of 5-HT at 5-HT$_3$ receptors is (±)-endo-4-amino-5-chloro-2-methoxy-N-(1-azabicyclo)-[3.3.1]-non-4-yl)benzamide, or a physiologically acceptable salt or solvate thereof, and wherein said H+K+ATPase inhibitor is omeprazole.

9. A method according to claim 5 wherein the compound which is an antagonist of 5-HT at 5-HT$_3$ receptors is a compound of formula (III) at a unit dose of 0.1 to 20 mg, which is administered in conjunction with the H+K+ATPase inhibitor at a unit dose of 5 to 250 mg.

10. A method according to claim 9 wherein (±)-endo-4-amino-5-chloro-2-methoxy-N-(1-azabicyclo)-[3.3.1]-non-4-yl)benzamide, or a physiologically acceptable salt or solvate thereof, is administered at a unit dose of 0.1 to 20 mg, and wherein omeprazole is administered at a unit dose of 5 to 250 mg.

* * * * *